United States Patent
Nicholas et al.

(10) Patent No.: US 10,633,355 B2
(45) Date of Patent: Apr. 28, 2020

(54) ORGANO-1-OXA-4-AZONIUM CYCLOHEXANE COMPOUNDS

(71) Applicant: UOP LLC, Des Plaines, IL (US)

(72) Inventors: Christopher P. Nicholas, Evanston, IL (US); Mark A. Miller, Niles, IL (US); Melissa M. Galey, Chicago, IL (US); Benjamin D. Yuhas, Evanston, IL (US); Sesh Prabhakar, Hoffman Estates, IL (US)

(*) Notice: Subject to any disclaimer, the term of this patent is extended or adjusted under 35 U.S.C. 154(b) by 0 days.

(21) Appl. No.: 15/981,084

(22) Filed: May 16, 2018

(65) Prior Publication Data

US 2018/0265485 A1 Sep. 20, 2018

Related U.S. Application Data

(60) Continuation-in-part of application No. 15/334,154, filed on Oct. 25, 2016, now abandoned, which is a division of application No. 14/561,132, filed on Dec. 4, 2014, now Pat. No. 9,522,896.

(51) Int. Cl.
| | | |
|---|---|---|
| *C07D 295/037* | (2006.01) | |
| *C07D 295/023* | (2006.01) | |
| *C07D 295/027* | (2006.01) | |
| *C07D 497/10* | (2006.01) | |

(52) U.S. Cl.
CPC ..... *C07D 295/037* (2013.01); *C07D 295/023* (2013.01); *C07D 295/027* (2013.01); *C07D 497/10* (2013.01)

(58) Field of Classification Search
CPC .................................................. C07D 295/037
See application file for complete search history.

(56) References Cited

U.S. PATENT DOCUMENTS 5,869,655 A 2/1999 Puckett et al.

FOREIGN PATENT DOCUMENTS

| EP | 0116203 | 8/1984 |
| JP | 2004264402 | 9/2004 |

OTHER PUBLICATIONS

Roufogalis, Potentiation of acetylcholinesterase by a series of quaternary ammonium compounds, J Pharm. Pharmac, 1968, 20, 135-145.
Booth, The Termal Decomposition of Quaternary Ammonium Hydroxides Part 5., Journal of the Chemical Society, Perkin Transation, Chemical Society, Letchworth GB, 1978 pp. 899-907 XP009092630.

*Primary Examiner* — Karen Cheng

(57) ABSTRACT

Novel 1-oxa-4-azonium cyclohexane salts are described. These compounds can be used as structure directing agents, and they overcome many of the typical problems associated with OSDA synthesis and subsequent zeolite synthesis. Methods for synthesis of the 1-oxa-4-azonium cyclohexane salts from a variety of starting materials are also described. A substituted hydrocarbon is added to water to form a mixture, and a 1-oxa-4-azacyclohexane derivative is then added. The reaction mixture stirred until a solution containing the 1-oxa-4-azonium cyclohexane salt is obtained.

6 Claims, 2 Drawing Sheets

ORGANO-1-OXA-4-AZONIUM CYCLOHEXANE COMPOUNDS

CROSS-REFERENCE TO RELATED APPLICATIONS

This application is a Continuation-In-Part of copending U.S. application Ser. No. 15/334,154 filed Oct. 25, 2016, which application is a Division of U.S. application Ser. No. 14/561,132 filed Dec. 4, 2014, now U.S. Pat. No. 9,522,896 issued Dec. 20, 2016, the contents of which cited applications are hereby incorporated by reference in their entirety.

BACKGROUND OF THE INVENTION

1. Field of the Invention

This invention relates to novel organo-1-oxa-4-azonium cyclohexane compounds, and a process for preparing the quaternary ammonium salts. The process involves forming 1-oxa-4-azoniumcyclohexane compounds from suitable reagents such as a substituted alkane and 1-oxa-4-azacyclohexane derivatives.

2. Description of the Related Art

Classes of molecular sieves include crystalline aluminophosphate, silicoaluminophosphate, or metalloaluminophosphate compositions which are microporous and which are formed from corner sharing $AlO_{4/2}$ and $PO_{4/2}$ tetrahedra. This class is described by Lok and coworkers in U.S. Pat. No. 4,440,871. Other classes of molecular sieves include crystalline aluminosilicate or silicate compositions, often referred to as zeolites. These are formed from corner sharing $SiO_{4/2}$ and $AlO_{4/2}$ tetrahedra. Numerous molecular sieves, both naturally occurring and synthetically prepared, are used in various industrial processes. Synthetically, these molecular sieves are prepared via hydrothermal synthesis employing suitable sources of Si, Al, P, and structure directing agents such as alkali metals, alkaline earth metals, amines, or organoammonium cations. The structure directing agents reside in the pores of the molecular sieve and are largely responsible for the particular structure that is ultimately formed. These species may balance the framework charge associated with silicon or other metals such as Zn in the aluminophosphate compositions or aluminum in the silicate compositions and can also serve as space fillers to stabilize the tetrahedral network framework. Molecular sieves are characterized by having pore openings of uniform dimensions, having a significant ion exchange capacity, and being capable of reversibly desorbing an adsorbed phase which is dispersed throughout the internal voids of the crystal without significantly displacing any atoms which make up the permanent molecular sieve crystal structure. Molecular sieves can be used as catalysts for hydrocarbon conversion reactions, which can take place on outside surfaces as well as on internal surfaces within the pore.

Synthesis of molecular sieve materials often relies on the use of organoammonium templates known as organic structure directing agents (OSDAs). While simple OSDAs such as tetramethylammonium, tetraethylammonium and tetrapropylammonium are commercially available, often, OSDAs are complicated molecules that are difficult and expensive to synthesize; however, their importance lies in their ability to impart aspects of their structural features to the molecular sieve to yield a desirable pore structure. For example, the synthesis of N,N,N,-trimethylmyrtanylammonium derivatives allowed the synthesis of CIT-1, a member of the CON zeotype (Lobo and Davis J. AM. CHEM. SOC. 1995, 117, 3766-79), the synthesis of a methyl substituted N,N,N',N'-tetraethylbicyclo[2.2.2]oct-7-ene-2,3,5,6-dipyrrolidinium diiodide enabled the synthesis of ITQ-37, the member of the ITV zeotype (Sun, et. al. NATURE, 2009, 458, 1154-7) and synthesis of the trans isomer of N,N-diethyl-2-methyldecahydroquinolinium iodide (Elomari, et. al. MICRO. MESO. MATER. 2009, 118, 325-33) allowed synthesis of SSZ-56, the member of the SFS zeotype. The use of 1,4,7,10,13,16-hexamethyl-1,4,7,10,13,16-hexaazacyclooctadecane as OSDA has been shown to allow synthesis of STA-7, an aluminophosphate based material of the SAV zeotype (Wright, et. al. J. CHEM. SOC., Dalton Trans., 2000, 1243-1248).

The art clearly shows that use of complex organoammonium SDAs often results in new molecular sieve materials. However, the synthesis of these complicated organoammonium compounds is quite lengthy and requires many steps, often in an organic solvent, thereby hindering development of the new molecular sieve material. Frequently, even for simple, commercially available OSDAs, the OSDA is the most costly ingredient used in synthesizing molecular sieve materials. Consequently, it would be economically advantageous to synthesize new molecular sieves from either commercially available organoammonium SDAs or SDAs which may be readily synthesized from commercially available starting materials.

The simple, commercially available, amine morpholine (tetrahydro-1,4-oxazine) has been previously utilized in aluminophosphate based molecular sieve synthesis and has been shown to yield CHA-type molecular sieves (Marchese, et. al. MICRO. MESO. MATER. 1999, 30, 145-53; Ito, et. al. ACTA CRYST. 1985, C41, 1698-1700), but has not yet been shown to yield other structure type molecular sieves. Additionally, the vapor pressure of morpholine is relatively high, making its use on commercial scale troublesome as low vapor pressure organoammonium SDAs are preferred.

The complicated OSDA(s) discussed previously were synthesized ex-situ and added to the reaction mixture at several points. However, one drawback of ex-situ synthesis is the process is typically carried out in the presence of an organic solvent, which necessitates at least one undesirable purification step to recover the SDA from the unwanted organic material.

Therefore, what is needed in the art are novel organo-1-oxa-4-azonium cyclohexane compounds. It would be desirable for these organo-1-oxa-4-azonium cyclohexane compounds to be useful as SDAs for aluminosilicate, silicate, aluminophosphate, or silicoaluminophosphate compositions.

SUMMARY OF THE INVENTION

The present invention discloses a process for preparing a pre-reacted aqueous solution of substituted hydrocarbons and amines essentially incapable of undergoing pyramidal inversion, which overcomes the aforementioned difficulties. The inventors have made the surprising discovery that a substituted hydrocarbon and amine may be reacted in an aqueous solution at (or slightly above) room temperature to yield an aqueous solution comprising the OSDA. This process is disclosed for a broad class of amines in U.S. application Ser. No. 14/552,654 filed Nov. 25, 2014, hereby incorporated by reference. This solution may then be used without purification in the synthesis of molecular sieves. This procedure thereby allows the preparation of SDAs, such as unusual quaternary ammonium salts, from readily available starting reagents in a facile and practical manner.

OSDAs prepared by the methods of the present invention are in aqueous solution and do not pose odor and flashpoint concerns. The result is the unprecedented ability to remove the cooling step typically required in the preparation of in-situ zeolite reaction mixtures and to avoid purification steps such as evaporation of organic solvent typically required in ex-situ preparation methods.

One aspect of the invention are novel morpholinium compounds comprising 1-oxa-4-azonium cyclohexane salts. In one version, the 1-oxa-4-azonium cyclohexane salts have the structure of Formula 1:

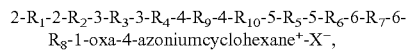

wherein $R_1$-$R_8$ are independently selected from H or an alkyl group having the formula $C_nH_{2n+1}$ where n is in the range from 1 to 4; $R_9$ and $R_{10}$ form a cyclic alkyl group having the formula $C_mH_{2m}$ forming a heterocycle of ring size q, where m is in the range from 4 to 8, and q is in the range of 5 to m+1; X is a halide or hydroxide; and the total number of C atoms in the molecule is in a range of 8 to 17.

In another aspect, the invention provides a method for synthesizing a 1-oxa-4-azonium cyclohexane compound. The method includes the steps of: (a) preparing an aqueous mixture comprising water, a substituted hydrocarbon and a 1-oxa-4-azacyclohexane derivative; (b) reacting the aqueous mixture; and (c) obtaining a solution comprising the organo-1-oxa-4-azoniumcyclohexane compound, wherein the mixture and the solution are essentially free of aluminum and silicon. In one version of the method, the solution is essentially free of aluminum, silicon and phosphorous. In one version of the method, the solution is essentially free of aluminum and phosphorous. Essentially free of is meant to indicate that the element described was not intentionally added to the mixture or solution. Adventitious amounts of the element may be permitted, whether coming from dissolution of reactor walls, impurities in the starting materials or other causes. Essentially free of may signify that less than 1 wt % or less than 0.5 wt % or less than 0.1 wt % of the element is present.

In one version of the method, the step of reacting the aqueous mixture occurs at a temperature from about 0° C. to about 125° C., and for a time from about 15 min to about 72 hours. In another version of the method, the organo-1-oxa-4-azoniumcyclohexane product is used as a structure directing agent in the synthesis of a molecular sieve. In another version of the method, the 1-oxa-4-azacyclohexane derivative is essentially incapable of undergoing pyramidal inversion.

It is therefore an advantage of the present invention to provide a system and method for preparing structure directing agents in an aqueous reaction mixture wherein the structure directing agents are prepared in the absence of Si and Al reactive sources. Furthermore, the aqueous mixture is capable of forming an organo-1-oxa-4-azoniumcyclohexane halogen salt such as a bromide salt, in order to ultimately provide a solution including a quaternary organoammonium compound. The organoammonium bromide salt can be ion-exchanged, either by reaction with $Ag_2O$ or by anion exchange resins to yield the hydroxide form of the organo-1-oxa-4-azoniumcyclohexane compound or used as the halogen salt directly. Finally, the resultant organoammonium compound can be used for the synthesis of a zeolite or molecular sieve.

These and other features, aspects, and advantages of the present invention will become better understood upon consideration of the following detailed description, drawings and appended claims.

DETAILED DESCRIPTION OF THE INVENTION

The present invention deals with an aqueous process for preparing novel 1-oxa-4-azonium cyclohexane salts. These compounds can be used as an organic structure directing agent (OSDA), and they overcome many of the typical problems associated with OSDA synthesis and subsequent zeolite synthesis. Embodiments of the present invention cover methods for synthesis of the 1-oxa-4-azonium cyclohexane salts from a variety of starting materials.

Figure 1:
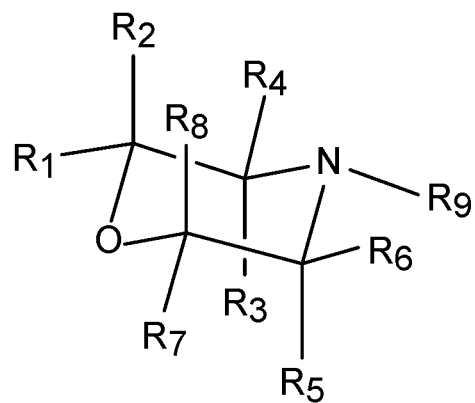
FIG. 1 is an illustration of the 1-oxa-4-azacyclohexane derivative.
Figure 2:
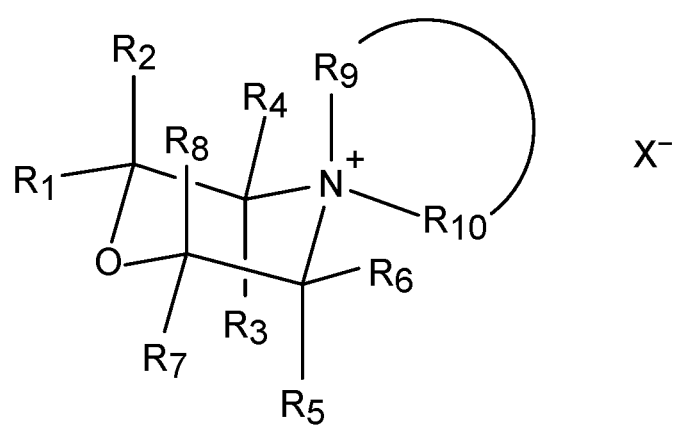
FIG. 2 is an illustration of the class of 1-oxa-4-azonium cyclohexane salts having the structure of Formula 1.

In a typical method for preparing the 1-oxa-4-azonium cyclohexane salts of the present invention, a substituted hydrocarbon is added to water to form a mixture. The 1-oxa-4-azacyclohexane derivative, as shown in FIG. 1, may then be added and the reaction mixture stirred until a solution containing the 1-oxa-4-azonium cyclohexane salt is observed. If the solution is cooled to room temperature, the product is stably maintained as an aqueous solution for later use.

In certain embodiments, the precursor reagents (e.g., the substituted alkane and 1-oxa-4-azacyclohexane derivative) may be added separately or together to form the reaction mixture at a number of points in the process. The precursors may be reacted together at temperatures ranging from about 0° C. to about 125° C. Preferably the precursors are reacted at about room temperature or at a slightly elevated temperature such as temperatures ranging from about 5° C. to about 100° C. More preferably, the precursors are reacted at temperatures from about 20° C. to about 120° C., or about 20° C. to about 80° C.

The reaction time varies from about 5 minutes to about 72 hours or from about 15 minutes to about 48 hours or from about 30 minutes to about 48 hours.

The resulting solution to may be cooled to room temperature or used as is. Other known techniques require the use of purification steps such as distillation, crystallization, chromatography and removal of a component via vacuum. A benefit of the instant method is that the solution of the organo-1-oxa-4-azoniumcyclohexane salt is prepared without additional purification steps occurring prior to use of the solution to make zeolites and molecular sieves. Some small laboratory scale procedures may involve removal of unreacted reactants; however, in commercial embodiments, it is most likely to react to completion. Ion-exchange as described below does not purify the solution, but converts halide anions to hydroxide ions and thus is not a purification step. The resulting solution may be cooled to room temperature or used as is. However, no purification steps occur prior to use of the solution.

In one aspect of the present invention, the 1-oxa-4-azonium cyclohexane salts are prepared from a substituted hydrocarbon and a 1-oxa-4-azacyclohexane derivative. Suitable substituted hydrocarbons include α,ω-dihalogen substituted alkanes having between 3 and 6 carbon atoms, di-halogen substituted alkanes having between 3 and 8 carbon atoms, and combinations thereof. Halogens include chlorine, bromine and iodine. In an aspect, the halogen is bromine or iodine. In another aspect, the halogen is bromine. In an aspect, the identity of the halogen substitutions on a substituted hydrocarbon may be all different, all the same, or any combination thereof.

α,ω-dihalogen substituted alkanes having between 3 and 6 carbon atoms include, but are not limited to, 1,3-dichloropropane, 1,4-dichlorobutane, 1,5-dichloropentane, 1,6-dichlorohexane, 1,3-dibromopropane, 1,4-dibromobutane, 1,4-dibromo-2-methylbutane, 1,5-dibromopentane, 1,6-dibromohexane, 1,3-diiodopropane, 1,4-diiodobutane, 1,5-diiodopentane, 1,6-diiodohexane and combinations thereof.

Di-halogen substituted alkanes having between 3 and 8 carbon atoms suitably include, but are not limited to, 1,2-dibromopropane, 1,3-dibromobutane, 1,3-dibromopentane, 1,4-dibromopentane, 2,4-dibromopentane, 1,5-dibromohexane, 1,4-dibromohexane, 1,3-dibromohexane, 2,4-dibromohexane, 2,5-dibromohexane, 2,5-dibromo-3-methylhexane, 2,5-dibromo-3,3-dimethylhexane, 1,4-dibromo-2-ethylbutane, and 1,2-dibromo-2-phenylethane. Halogen substitutions may be chlorine, bromine or iodine, but are illustrated for bromine. In an aspect, the two halogen substitutions may be the same or different.

Halogen substitutions may be chlorine, bromine or iodine, but are illustrated for bromine. In an aspect, the identity of the three halogen substitutions on the substituted hydrocarbon may be all different, all the same, or any combination thereof.

In an aspect, the mole ratio of the 1-oxa-4-azacyclohexane derivative to the substitution is from 1:1 to 2:1 and is preferably from 1:1 to 1.5:1. Typically, the mole ratio of 1-oxa-4-azacyclohexane derivative to substitution is approximately 1. Thus, when butylbromide is used as the substituted hydrocarbon, approximately 1 equivalent of 1-oxa-4-azacyclohexane derivative is typically used, whereas when 1,4-dibromobutane is used as the substituted hydrocarbon, approximately 2 equivalents of 1-oxa-4-azacyclohexane derivative are typically used.

Figure 3A:
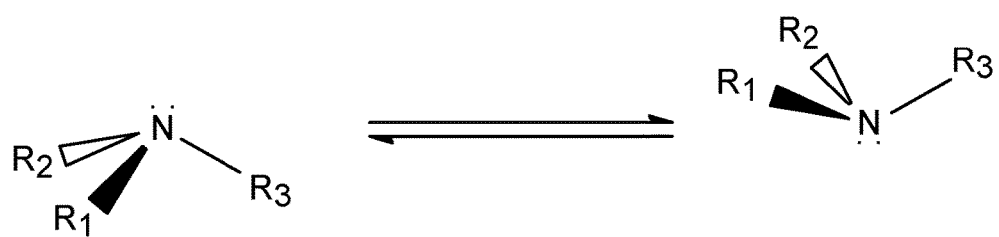
FIGS. 3A and 3B are illustrations of substituted amine compounds undergoing pyramidal inversion.
Figure 3B:
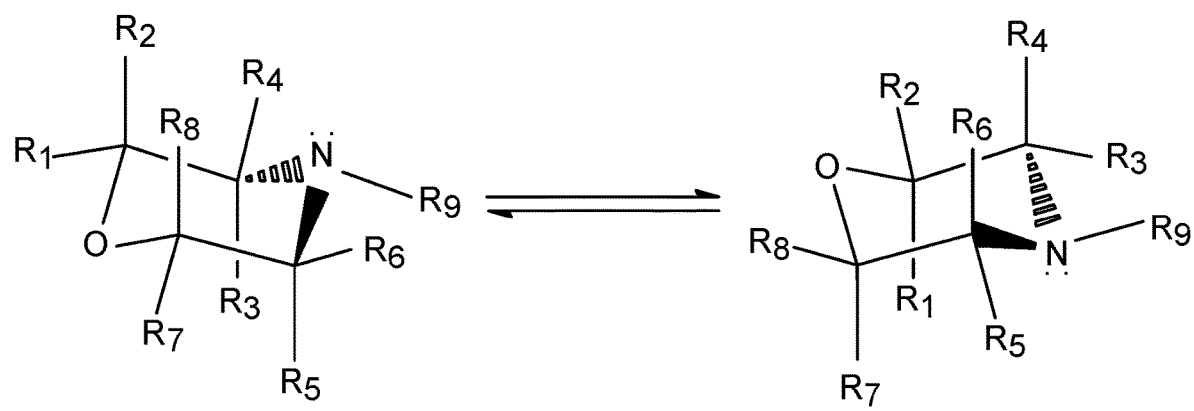

Suitable 1-oxa-4-azacyclohexane derivatives include those for which at least one conformer is essentially incapable of undergoing pyramidal inversion. The IUPAC definition of pyramidal inversion is given as, "a polytopal rearrangement in which the change in bond directions to a three-coordinate central atom having a pyramidal arrangement of bonds (tripodal arrangement) causes the central atom (apex of the pyramid) to appear to move to an equivalent position on the other side of the base of the pyramid. If the three ligands to the central atom are different pyramidal inversion interconverts enantiomers." The tripodal nature of many nitrogen compounds result in the ability of these compounds to undergo pyramidal inversion. Typically, the energy barrier to inversion is low for unconstrained molecules. For example, ammonia ($NH_3$) has an inversion barrier of 24.5 kJ mol$^{-1}$, with an observed inversion frequency of about $2.4*10^{10}$ s$^{-1}$, dimethylamine has an inversion barrier of 18 kJ mol$^{-1}$, triisopropylamine has an inversion barrier of 6-8 kJ mol$^{-1}$ and dimethylethylamine has an inversion barrier of 22 kJ mol$^{-1}$. However, inversion barrier energy can become very high when the nitrogen substituents are part of a small ring or other rigid molecule as in the case of 1-methylpyrrolidine. Molecules defined as essentially incapable of undergoing pyramidal inversion have an inversion barrier energy of at least about 28 kJ mol$^{-1}$ and more preferably of at least about 30 kJ mol$^{-1}$. A discussion of pyramidal inversion may be found in Rauk, A., et al., (1970), Pyramidal Inversion. ANGEW. CHEM. INT. ED. ENGL., 9: 400-414, with further discussion specifically for amines found in INORGANIC CHEMISTRY edited by Arnold F. Holleman, et al., Academic Press, 2001. Furthermore, FIGS. 3A-B illustrate substituted amine compounds undergoing pyramidal inversion. Molecules may exist in many conformers or folding patterns. For example, it is well known that both chair and boat forms of cyclohexane exist and interconvert between the two different conformers. In an aspect of the invention, at least one conformer of the amine is essentially incapable of undergoing pyramidal inversion.

TABLE 1

Molecules generally incapable of undergoing pyramidal inversion.

| Molecule Name | Inversion Barrier (kJ mol$^{-1}$) |
| --- | --- |
| N-methylhomopiperidine | 28-29 |
| 1-methyl-4-piperidone | 30.7 |
| Trimethylamine | 31-35 |
| 1,3,3-trimethylpyrrolidine | 31 |
| N-methylpyrrolidine | 31-35 |
| 3-methyl-1-thia-3-azacyclopentane | 33 |
| 9-methyl-9-azabicyclo[3.3.1]nonane | 34 |
| N-methyl piperidine (equatorial) | 36.4 |
| 1,2,2,6-tetramethylpiperidine (axial) | 38 |
| 2-methyl-dihydro-2-azaphenalene | 40.5 |
| Methylazetidine | 42 |
| 1,2,2,6-tetramethylpiperidine (equitorial) | 46 |
| 4-methyl-1-oxa-4-azacyclohexane AKA methylmorpholine | 48 |
| 2-methyl-1-oxa-2-azacyclohexane (equitorial) | 57 |
| 2-methyl-1-oxa-2-azacyclopentane | 65 |
| Methylaziridine | 80-90 |

The 1-oxa-4-azacyclohexane derivative is illustrated in FIG. 1 and has the structure of formula 2:

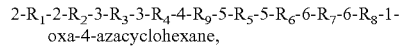

2-$R_1$-2-$R_2$-3-$R_3$-3-$R_4$-4-$R_9$-5-$R_5$-5-$R_6$-6-$R_7$-6-$R_8$-1-oxa-4-azacyclohexane, wherein $R_1$-$R_9$ are independently selected from H or an alkyl group having the formula $C_nH_{2n+1}$, and the total number of C atoms in the molecule is in the range of 4 to 12.

In some versions, $R_1$-$R_9$ are H.

In some versions, at least one of $R_1$-$R_9$ is an alkyl group. In some versions, at least two of $R_1$-$R_9$ are alkyl groups. In some versions, when at least two of $R_1$-$R_9$ are alkyl groups, two of the alkyl groups are on the same C atom (e.g., $R_1$ and $R_2$, or $R_3$ and $R_4$, or $R_5$ and $R_6$, or $R_7$ and $R_8$).

Where more than one alkyl group is present, the alkyl groups can be the same group or they can be different. Most commonly, the alkyl groups are methyl or ethyl groups.

Suitable 1-oxa-4-azacyclohexane derivatives include, but are not limited to, 4-butylmorpholine, 4-propylmorpholine, 4-ethylmorpholine, 4-methylmorpholine, morpholine, 2-methylmorpholine, 2,4-dimethylmorpholine, 4-ethyl-2-methylmorpholine, 4-propyl-2-methylmorpholine, 3-methylmorpholine, 3,4-dimethylmorpholine, 4-ethyl-3-methylmorpholine, 4-propyl-3-methylmorpholine, 5-methylmorpholine, 2,5-dimethylmorpholine, 4-ethyl-5-methylmorpholine, 4-propyl-5-methylmorpholine, 5-ethyl-2-methylmorpholine, 6-methylmorpholine, 4,6-dimethylmorpholine, 4-ethyl-6-methylmorpholine, 4-propyl-6-methylmorpholine, 2,6-dimethylmorpholine, 2,4,6-trimethylmorpholine, 4-ethyl-2,6-dimethylmorpholine, 2,3-dimethylmorpholine, 2,3,4-trimethylmorpholine, 4-ethyl-2, 3-dimethylmorpholine, 2,5-dimethylmorpholine, 2,4,5- trimethylmorpholine, 4-ethyl-2,5-dimethylmorpholine, 2,2-dimethylmorpholine, 2,2,4-trimethylmorpholine, 4-ethyl-2,2-dimethylmorpholine, 3,3-dimethylmorpholine, 3,3,4-trimethylmorpholine, 4-ethyl-3,3-dimethylmorpholine, 5,5-dimethylmorpholine, 4,5,5-trimethylmorpholine, 4-ethyl-5,5-dimethylmorpholine, 6,6-dimethylmorpholine, 4,6,6-trimethylmorpholine, 4-ethyl-6,6-dimethylmorpholine, 5-ethyl-2-methylmorpholine and combinations thereof. Butyl may indicate n-butyl, sec-butyl, isobutyl or tert-butyl. Propyl may indicate n-propyl or isopropyl.

The 1-oxa-4-azacyclohexane derivative includes $R_1$-$R_9$, and at least $R_{10}$ is from the substituted hydrocarbon. In some versions, the substituents at $R_1$-$R_8$ of the 1-oxa-4-azacyclohexane derivative and the substituents at $R_1$-$R_8$ of the 1-oxa-4-azoniumcyclohexane salt are the same. In some versions, the substituents at $R_1$-$R_9$ of the 1-oxa-4-azacyclohexane derivative and the substituents at $R_1$-$R_9$ of the 1-oxa-4-azoniumcyclohexane salt are the same.

One class of 1-oxa-4-azoniumcyclohexane salts have the structure of Formula 1:

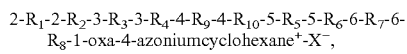

wherein $R_1$-$R_8$ are independently selected from H or an alkyl group having the formula $C_nH_{2n+1}$ where n is in the range from 1 to 4; $R_9$ and $R_{10}$ form a cyclic alkyl group having the formula $C_mH_{2m}$ forming a heterocycle of ring size q, where m is in the range from 4 to 8, and q is in the range of 5 to m+1; X is a halide or hydroxide; and the total number of C atoms in the molecule is in a range of 8 to 17.

In some versions, when $R_1$-$R_8$ are H, and m is 4, X is hydroxide. In some versions, when $R_1$-$R_8$ are H, m is in the range from 5 to 8.

In some versions, X is hydroxide.

The cyclic alkyl group can have from 4 to 8 carbons, and the heterocycle ring has a ring size of 5 to m+1. Most commonly, the heterocycle ring has 5 or 6 members. In some versions, q is 5. In some versions q is 6. In some versions, q is 5 or 6.

In some versions, $R_{10}$ can be a straight chain alkyl group or a branched alkyl group. When $R_{10}$ is a branched alkyl group, the heterocycle ring can have one or more alkyl substituents. For example, the use of 1,4-dibromo-4,4-dimethylbutane would yield a 5 member heterocycle ring with 2 methyl groups on the carbon adjacent to the nitrogen atom and the cyclic alkyl group has the formula $C_6H_{12}$.

In some versions, $R_1$-$R_8$ are H.

In some versions, at least one of $R_1$-$R_8$ is an alkyl group. In some versions, at least two of $R_1$-$R_8$ are alkyl groups. In some versions, when at least two of $R_1$-$R_8$ are alkyl groups, two of the alkyl groups are on the same C atom (e.g., $R_1$ and $R_2$, or $R_3$ and $R_4$, or $R_5$ and $R_6$, or $R_7$ and $R_8$).

Where more than one alkyl group is present, the alkyl groups can be the same group or they can be different. Most commonly, the alkyl groups are methyl or ethyl groups.

In one version, the cyclic alkyl group has 5 carbons, q is 6, $R_1$-$R_8$ are H, and X is a halide.

The 1-oxa-4-azonium cyclohexane halide salt can be ion-exchanged, either by reaction with $Ag_2O$ yielding AgX as a byproduct or by passage across anion exchange resins to yield the hydroxide form of the 1-oxa-4-azonium cyclohexane compound or used as the halogen salt directly.

The ion-exchange process may involve contacting the 1-oxa-4-azonium cyclohexane halide salt with an ion-exchange resin having hydroxide ions. A particular ion-exchange resin capable of converting halide ions to hydroxide ions is Dowex Monosphere 550A UPW, available from Dow Chemical. The ion exchange may take place at temperatures from about 20° C. to about 85° C. or from about 20° C. to about 50° C. or from about 25° C. to about 40° C. for times from about 15 minutes to about 8 hours or from about 30 minutes to about 6 hours or from about 30 minutes to about 3 hours. The ion exchange may be performed in continuous or batch mode or any combination thereof. Batch mode is preferred when using $Ag_2O$ and continuous mode is preferred when using ion exchange resin. Individual 1-oxa-4-azonium cyclohexane halide salts may require different operating conditions for the ion exchange from halide to hydroxide. Depending on the interaction of anion with the 1-oxa-4-azonium cyclohexane cation, ion-exchange may be difficult or impossible.

Comparing the $^{13}C$ chemical shifts for the bromide and hydroxide salts in Example 2 and Example 3 shows that the interaction of the 1-oxa-4-azonium cyclohexane salt with the anion varies with the identity of the anion. In particular, without wishing to be bound to theory, the chemical potential of the C atom next to the cationic N center is particularly affected. The electron density of the salt can be greatly affected by the identity of the anion. This difference can greatly affect the ability of the 1-oxa-4-azonium cyclohexane anion salt to direct the synthesis of particular zeolites or molecular sieves. In molecular sieve synthesis, hydroxide is typically used as a mineralizing agent, so hydroxide SDA salts are often preferred to halide SDA salts. Utilizing the 1-oxa-4-azonium cyclohexane anion salt as a hydroxide salt also allows the separation of hydroxide to T-atom ratio, an important molecular sieve synthesis parameter, from metal to T-atom ratio as metal ions such as sodium are no longer introduced on a 1:1 mole basis with hydroxide. T-atom is used to represent the elements in tetrahedral framework positions, typically silicon, phosphorous or aluminum.

EXAMPLES

In order to more fully illustrate the invention, the following examples are set forth. It is to be understood that the examples are only by way of illustration and are not intended as a limitation on the broad scope of the invention as set forth in the appended claims.

Example 1

422.44 g water was weighed into a 2 L Teflon bottle, and the bottle was placed in a 4 L beaker. Under constant stirring, 218.1 g 1,4 dibromobutane, 99% was added to the water. To this mixture, 204.34 g 4-Methylmorpholine, 99% was added. Approximately 1.5 L tap water was placed in the 4 L beaker surrounding the Teflon bottle to help control the heat of reaction. Low heat, approximately 50° C., was used to warm up the mixture. Stirring was continued until a yellow solution was formed and no clear additional phase was present. $^{13}C$ NMR of the solution showed a ratio of 1 mole methylmorpholine to 2.83 moles 1,4-bis(4-methylmorpholinium)butane dibromide.

Example 2

413 g water was weighed into a 2 L Teflon bottle. 474.1 g. 1,5 Dibromopentane, 97% (2 moles) was added. To this mixture, 176 g. Morpholine, 99% (4 moles) was added while stirring. The water and morpholine combined to form a cloudy phase while the denser dibromopentane remained on the bottom. The Teflon bottle was moved into a 4 liter beaker as secondary containment and placed under a high speed overhead stirrer for stirring at room temperature. Approximately 1-1.5 liters of cool water were added to the 4 liter beaker to disperse a strong exotherm should one occur. At about 15 minutes, the mixture began to turn yellow, indicating the reaction was beginning. The exotherm was mild. After an hour, the result was a clear light orange "solution". The remaining 413 g water was mixed in to make the final solution. $^{13}$C nuclear magnetic resonance (NMR) was used to confirm that the product comprises a 3-oxa-6-azoniaspiro [5.5]undecane bromide solution. Peaks for the spirocyclic compound were observed at 63.6, 59.9, 58.0, 21.0, and 18.9 ppm with respect to tetramethylsilane. Resonances for morpholinium were present at 59.9 and 43.4 ppm. The ratio of spirocyclic compound to morpholinium was 1:1. Variable temperature NMR, with C—N splitting is required to identify both compounds and acquire the proper integration ratios. The starting material 1,5-dibromopentane has peaks at 29.3, 34.4, and 36.2 ppm with integral ratios of 1:2:2 respectively which is not observed in the final solution.

Example 3

1150 grams of the solution from Example 2 was contacted with 336.4 grams of Ag$_2$O in a round-bottom flask, which combined to form a grey opaque solution. The flask was placed under a high speed overheard stirrer for stirring at room temperature (open system) for 1 day. The sample was filtered to remove the precipitated silver bromide and the final solution was sent for water analysis which showed that the sample was composed of 64.6% water. $^{13}$C nuclear magnetic resonance (NMR) was used to confirm that the product comprises a 3-oxa-6-azoniaspiro[5.5]undecane hydroxide solution. Peaks for the spirocyclic compound were observed at 67.1, 60.0, 57.9, 20.9, and 18.7 ppm with respect to tetramethylsilane. Resonances for morpholinium were present at 59.8 and 44.7 ppm. The ratio of spirocyclic compound to morpholinium was about 1:1. Comparing the $^{13}$C chemical shifts for the bromide and hydroxide salts in Example 2 and Example 3 shows that the interaction of the 1-oxa-4-azonium cyclohexane salt with the anion varies with the identity of the anion. In particular, without wishing to be bound to theory, the chemical potential of the C atom next to the cationic N center is particularly affected. The electron density of the salt can be greatly affected by the identity of the anion.

Example 4

88.65 g water was weighed into a 1 L Teflon bottle. 141.33 g 1,4-Dibromobutane, 99% was added. To this mixture, 154 g 4-Ethylmorpholine, 97% was added. The water and ethylmorpholine combined to form a cloudy phase while the denser dibromobutane remained on the bottom. The Teflon bottle was moved into a 2 liter beaker as secondary containment and placed under a high speed overhead stirrer for stirring at room temperature. The Teflon bottle was sealed and placed at 100° C. overnight with no stirring. After the solution was cooled back down to room temperature, 88 g of deionized water was added to the solution. The solution was again placed at 100° C. overnight with no stirring and the result was a brown translucent solution which, by $^{13}$C NMR contained peaks for 1,4-bis(4-ethylmorpholinium) butane dication. The sample was sent for water analysis which showed that it was composed of 36.6% water.

Example 5

355.88 g water was weighed into a 2 L glass beaker. 355.57 g 1,5-Dibromopentane, 97% (1.5 moles) was added.

To this mixture, 356.19 g 4-Ethylmorpholine, 97% (3 moles) was added. The water and ethylmorpholine combined to form a cloudy phase while the denser dibromopentane remained on the bottom. The glass beaker was moved onto a hot plate with low heat and placed under a high speed overhead stirrer for stirring at room temperature. The solution was then transferred into a 2 L Teflon bottle, which was sealed and placed at 100° C. overnight with no stirring. After cooling, the solution as placed into a 2 L Parr autoclave and heated to 100° C. for 4 hours. 355.88 g of deionized water was then added to obtain a 50% solution.

Example 6

196.5 g, water was weighed into a 2 L Teflon bottle. 254.14 g 1,6-Dibromohexane, 96% was added. To this mixture, 204.34 g 4-Methylmorpholine, 99% was added. The water and morpholine combined to form a cloudy phase while the denser dibromohexane remained on the bottom. The solution was put in a 4 liter beaker as secondary containment and placed under a high speed overhead stirrer for stirring at room temperature. The solution was then transferred into a 2 L Parr autoclave, which was sealed and placed at 125° C. overnight with no stirring. 261.9 g deionized water was then added to obtain a 50% solution and the sample was placed back into the 2 L Parr autoclave at 125° C. overnight. The result was a brown clear solution. $^{13}$C NMR showed peaks at 65.5, 60.6, 59.7, 47.0, 25.3, and 21.1 ppm in a 1:2:2:1:1:1 ratio for 1,6-bis (4-Methylmorpholinium)hexane dibromide and peaks at 64.9, 53.9, and 44.5 ppm in a 2:2:1 ratio for starting material 4-methylmorpholine. The ratio of diquaternary compound to amine was 1:0.9.

Example 7

439 grams of the solution from Example 4 was contacted with 147.5 grams of Ag$_2$O in a round-bottom flask, which combined to form a grey opaque solution. The flask was placed under a high speed overheard stirrer for stirring at room temperature for 1 day. The sample was filtered to remove the precipitated silver bromide and the final solution was sent for water analysis which showed that the sample was composed of 67.0% water.

Example 8

1257 grams of the solution from Example 5 was contacted with 324.26 grams of Ag$_2$O in a round-bottom flask, which combined to form a grey opaque solution. The flask was placed under a high speed overheard stirrer for stirring at room temperature for 1 day. The sample was filtered to remove the precipitated silver bromide and the final solution was sent for water analysis which showed that the sample was composed of 65.9% water.

Example 9

1116 grams of the solution from Example 6 was contacted with 295.64 grams of Ag$_2$O in a round-bottom flask, which combined to form a grey opaque solution. The flask was placed under a high speed overheard stirrer for stirring at room temperature for 1 day. The sample was filtered to remove the precipitated silver bromide and the final solution was sent for water analysis which showed that the sample was composed of 60.9% water.

Example 10

25.73 g water was weighed into a 125 mL Teflon bottle. 12.57 g 1,4-Dibromobutane, 99% was added. To this mixture, 13.15 g 2,6-Dimethylmorpholine, 97.1% was added while stirring. The water and 2-6-dimethylmorpholine combined to form a cloudy phase while the denser dibromobutane remained on the bottom. The Teflon bottle was moved into a 400 mL beaker as secondary containment and placed on a hot plate for stirring under low heat while sealed, approximately 90° C. After two days, the result was a clear light yellow solution. The sample was sent for $^{13}$C NMR. The 1-oxa-4-azonium cyclohexane derivative 2,6-dimethylmorpholine is comprised of two compounds, A having peaks at 75.5, 55.1, and 21.9 ppm with 1:1:1 ratios and B having peaks at 69.1, 54.2, and 20.5 ppm with 1:1:1 ratios. The ratio of the two compounds is 2.75A to 1B. The yellow solution has peaks at 16.4, 17.2, 17.3, 17.7, 20.6, 21.0, 21.7, 46.5, 47.2, 59.4, 61.7, 63.0, 63.9, 64.0, 65.7, 68.1, 68.3 and 69.8 ppm with integral ratios of 1.25, 1.75, 3.7, 4, 1.2, 4.1, 2, 1.8, 4.35, 1.3, 1.5, 1.8, 4, 1.95, and 4 respectively. Without wishing to be bound by theory, it is believed that compounds A and B in the morpholine derivative are the cis and trans forms of the 2,6-dimethylmorpholine and peaks in the product are due to multiple conformers of cis and trans substituted dimethylmorpholine based salts.

Example 11

591.15 g water was weighed into a 2 L Teflon bottle. 436.21 g 1,4-Dibromobutane, 99% (2 moles) was added. To this mixture, 352.0 g Morpholine, 99% (4 moles) was added while stirring. The water and morpholine combined to form a cloudy phase while the denser dibromobutane remained on the bottom. The Teflon bottle was moved into a 4 liter beaker as secondary containment and placed under a high speed overhead stirrer for stirring at room temperature. Approximately 0.5-1 liters of cool water were added to the 4 liter beaker to disperse a strong exotherm should one occur. After 1.5-2.5 hours, the result was a clear light yellow solution. An additional 197.05 g water was mixed in to form the final solution. $^{13}$C nuclear magnetic resonance (NMR) was used to confirm that the product was a 8-oxa-5-azoniaspiro[4.5] decane bromide solution. Peaks for the spirocyclic compound were observed at 63.3, 62.3, 59.2, and 21.4 ppm with respect to tetramethylsilane with integral ratios of 2:2:2:2 respectively. Resonances for morpholinium were present at 63.9 and 43.5 ppm with integral ratios of 2:2. The ratio of spirocyclic compound to morpholinium was 1:1. The presence of both compounds was confirmed by ion chromatography/mass spectrometry. The starting material 1,4-dibromobutane has peaks in the $^{13}$C NMR at 33.5 and 35.5 ppm. Peaks due to the dibromobutane were not observed in the final solution.

Example 12

1200 grams of the solution from Example 6 was contacted with 365.5 grams of Ag$_2$O in a round-bottom flask, which combined to form a grey opaque solution. The flask was placed under a high speed overheard stirrer for stirring at room temperature for 1 day. The sample was filtered to remove the precipitated silver bromide and the final solution was sent for water analysis which showed that the sample was composed of 67.3% water.

Although the invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

The invention claimed is:

1. A morpholinium compound comprising a 1-oxa-4-azonium cyclohexane salt having a structure of:

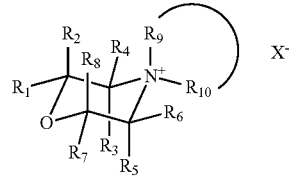

Formula 1

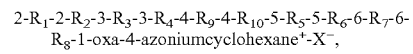

2-R$_1$-2-R$_2$-3-R$_3$-3-R$_4$-4-R$_9$-4-R$_{10}$-5-R$_5$-5-R$_6$-6-R$_7$-6-R$_8$-1-oxa-4-azoniumcyclohexane$^+$-X$^-$, wherein R$_1$-R$_8$ are independently selected from H or an alkyl group having the formula C$_n$H$_{2n+1}$ where n is in the range from 1 to 4; at least one of R$_1$-R$_8$ is an alkyl group; R$_9$ and R$_{10}$ form a cyclic alkyl group having the formula C$_m$H$_{2m}$ forming a heterocycle of ring size q, where m is in the range from 4 to 8, and q is in the range of 5 to m+1; X is hydroxide; and the total number of C atoms in the molecule is in a range of 8 to 17.

2. The morpholinium compound of claim 1 having the Formula 1, wherein at least two of R$_1$-R$_8$ are an alkyl group.

3. The morpholinium compound of claim 1 having the Formula 1, wherein at least two of R$_1$-R$_8$ are an alkyl group, and wherein at least two of R$_1$-R$_8$ are the same alkyl group.

4. The morpholinium compound of claim 1 having the Formula 1, wherein at least two of R$_1$-R$_8$ are an alkyl group and the at least two of the alkyl groups are on the same C atom.

5. A morpholinium compound comprising a 1-oxa-4-azonium cyclohexane salt having a structure of:

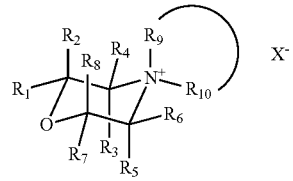

Formula 1

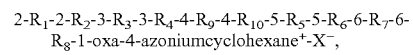

2-R$_1$-2-R$_2$-3-R$_3$-3-R$_4$-4-R$_9$-4-R$_{10}$-5-R$_5$-5-R$_6$-6-R$_7$-6-R$_8$-1-oxa-4-azoniumcyclohexane$^+$-X$^-$, wherein R$_1$-R$_8$ are independently selected from H or an alkyl group having the formula C$_n$H$_{2n+1}$ where n is in the range from 1 to 4; R$_9$ and R$_{10}$ form a cyclic alkyl group having the formula C$_m$H$_{2m}$ forming a heterocycle of ring size q, where m is in the range from 4 to 8, and q is in the range of 5 to m+1; X is a halide or hydroxide; and the total number of C atoms in the molecule is in a range of 13 to 17.

6. A morpholinium compound comprising a 1-oxa-4-azonium cyclohexane salt having a structure of:

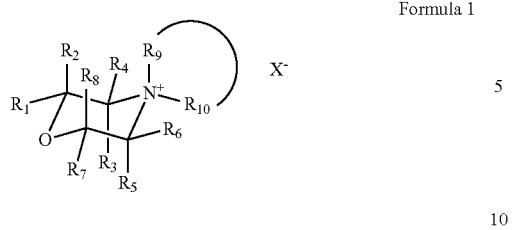

Formula 1

2-$R_1$-2-$R_2$-3-$R_3$-3-$R_4$-4-$R_9$-4-$R_{10}$-5-$R_5$-5-$R_6$-6-$R_7$-6-$R_8$-1-oxa-4-azoniumcyclohexane$^+$-X$^-$, wherein $R_1$-$R_8$ are independently selected from H or an alkyl group having the formula $C_nH_{2n+1}$ where n is in the range from 1 to 4; $R_9$ and $R_{10}$ form a cyclic alkyl group having the formula $C_mH_{2m}$ forming a heterocycle of ring size q, where m is in the range from 4 to 8, and q is 5 or 6; X is hydroxide; and the total number of C atoms in the molecule is in a range of 10 to 17.

* * * * *